US006458577B1

United States Patent
Huang

(10) Patent No.: US 6,458,577 B1
(45) Date of Patent: Oct. 1, 2002

(54) METHODS OF CULTURING AND ASSAYING A VIRUS IN A SPECIMEN AND COMPOSITIONS AND CELL LINES FOR DOING THE SAME

(75) Inventor: Yung T. Huang, Richmond Heights, OH (US)

(73) Assignee: University Hospital of Cleveland, Cleveland, OH (US)

( * ) Notice: Subject to any disclaimer, the term of this patent is extended or adjusted under 35 U.S.C. 154(b) by 0 days.

(21) Appl. No.: 08/860,305

(22) PCT Filed: Dec. 27, 1996

(86) PCT No.: PCT/US96/20827

§ 371 (c)(1),
(2), (4) Date: Dec. 1, 1997

(87) PCT Pub. No.: WO97/24461

PCT Pub. Date: Jul. 10, 1997

(51) Int. Cl.$^7$ .............................. C12N 7/01; C12N 7/02
(52) U.S. Cl. .................... 435/235.1; 435/235; 435/239; 435/243
(58) Field of Search ............................ 435/5, 243, 7.2, 435/239, 235, 325

(56) References Cited

U.S. PATENT DOCUMENTS

| | | | | |
|---|---|---|---|---|
| 3,616,203 | A | 10/1971 | Brown | 195/1.8 |
| 4,460,690 | A | 7/1984 | Ogilvie | 435/235 |
| 5,891,624 | A | 4/1999 | Huang | 435/5 |
| 5,939,253 | A | 8/1999 | Scholl et al. | 435/5 |

FOREIGN PATENT DOCUMENTS

WO      8906686      7/1989

OTHER PUBLICATIONS

PA Baeuerle (1991) Biochim et Biophys Acta 1072: 63–80.*
N Miller et al (1994) Parasitology Today 10: 92–97.*
RA Stull et al (1995) Pharmaceutical Research 12: 465–483.*
S Wu–Pong (1994) Pharmaceutical Technology 118: 102–114.*
RW Wagner (1994) Nature 372: 333–335.*
Roubal, et al. : Effect of n–butyrate on superinfection of raji lymphoblastoid cell line by epstein barr virus: Acta Virol. : vol. 29: pp. 162–165.
Boshart et al., "A Very Strong Enhancer Is Located Upstream of an Immediate Early Gene of Human Cytomegalovirus," Cell 41:521–530 (1985).
Dijkema et al., "Cloning and Expression of the Chromosomal Immune Interferon Gene of the Rat," EMBO J. 4:761–767 (1985).
Gorman et al., "The Rous Sarcoma Virus Long Terminal Repeat is a Strong Promoter When Introduced into a Variety of Eukaryotic Cells y DNA–mediated Transfection," Proc. Natl. Acad. Sci. USA 79:6777–6781 (1982).

Kim et al., "Use of the human elongation factor 1α promoter as a versatile and efficient expression system," Gene 91:217–223 (1990).
Leland in Clinical Virology, W.B. Saunders Company, Philadelphia, PA at pp. 60–65, and 85–86 (1996).
Maniatis et al., "Regulation of Inducible and Tissue–Specific Gene Expression," Science 236:1237 (1987).
Mizushima and Nagata, "pEF–BOS, a powerful mammalian expression vector," Nuc. Acids. Res. 18:5322 (1990).
Olsen et al., "Isolation of Seven Respiratory Viruses in Shell Vials: a Practical and Highly Sensitive Method," J. Clin. Microbiol. 31:422–425 (1993).
Rabalais et al., "Rapid Diagnosis of Respiratory Viral Infections by Using a Shell Vial Assay and Monoclonal Antibody Pool," J. Clin. Microbiol. 30:1505–1508 (1992).
Sambrook et al., *Molecular Cloning: A Laboratory Manual*, 2nd ed., Cold Spring Harbor Laboratory Press, New York, pp. 16.6–16.15 (1989).
Schmidt and Emmons, "General Principles of Laboratory Diagnostic Methods for Viral, Rickettsial, and Chlamydial Infections," in Schmidt and Emmons (eds.), Diagnostic Procedures for Viral, Rickettsial and Chlamydial Infections, American Public Health Association, Washington, D.C., p. 4 (1989).
Smith et al., "Detection of Respiratory Syncytial virus in Nasopharyngeal Secretions by Shell Vial Technique," J. Clin. Microbiol. 29:463–465 (1991).
Uetsuki et al., "Isolation and Characterization of the Human Chromosomal Gene for Polypeptide Chain Elongation Factor–1α," J. Biol. Chem. 264:5791–5798 (1989).
Voss et al., "The role of enhancers in the regulation of cell–type–specific transcriptional control," Trends Biochem. Sci. 11:287–289 (1986).
Wiedbrauk and Johnston, Manual of Clinical Virology, Raven Press, Inc., New York, NY, pp. 1–17, and 64–76 (1993).
Pinto et al. (1994) "Use of the Colonic Carcinoma Cell Line CaCo–2 for In Vivo Amplification and Detection of Enteric Viruses," J. Medical Virol. 44:310–315.

(List continued on next page.)

Primary Examiner—Laurie Scheiner
(74) Attorney, Agent, or Firm—Renner, Otto, Boisselle & Sklar, LLP

(57) ABSTRACT

This invention relates to a method for culturing a virus including the steps of: (A) providing cells from a cell line susceptible to infection by the virus and a specimen; (B) treating the cells with a compound of formula RC(O)Q, wherein Q is R, OR, OX or X, each R is independently hydrogen or a hydrocarbyl group containing 1 to about 10 carbon atoms and wherein X is hydrogen or a cation; © inoculating the treated cells with the specimen; and (D) incubating the inoculated cells to allow viral growth to proceed.

8 Claims, No Drawings

OTHER PUBLICATIONS

Dagan and Menegus, "A combination of four cell types for rapid detection of enteroviruses in clinical specimens," J. Med. Virol. 19:219–228 (1986).

Chonmaitree et al., "Comparison of Cell Cultures for Rapid Isolation of Enteroviruses," J. Clin. Microbiol. 26:2576–2580 (1988).

Castells et al., "NCI–H292 as an Alternative Cell Line for the Isolation and Propagation of the Human Paramyxoviruses," Arch. Virol. 115:277–288 (1990).

Brumback and Wade, "Simultaneous Rapid Culture for Four Respiratory Viruses in the Same Cell Monolayer Using a Differential Multicolored Fluorescent Confirmatory Stain," J. Clin. Microbiol. 34:798–801 (1996).

Gleaves et al., "Detection of Human Cytomagalovirus in Clinical Specimens by Centrifugation Culture with a Non-human Cell Line," J. Clin. Microbiol. 30:1045–1048 (1992).

Hierholzer et al., "Sensitivity of NCI–H292 Human Lung Mucoepidermoid Cells for Respiratory and Other Human Viruses," J. Clin. Microbiol. 30:1504–1510 (1993).

Klespies et al., "Detection of enteroviruses from clinical specimens by spin amplification shell vial culture and monoclonal antibody assay," J. Clin. Microbiol. 34:1465–1467 (1996).

Leonardi et al., "Use of Continuous Human Lung Cell Culture for Adenovirus Isolation," Intervirology 38:352–355 (1995).

ViroMED Laboratories, Inc. Pamphlet entitled, *"ViroMed Cell Culture Products"* (1996).

Benton & Hurst (1986) "Evaluation of mixed cell types and 5–iodo–2'–deoxyuridine treatment upon plaque assay titers of human enteric viruses," Applied and Environmental Microbiology, May issue, p1036–1040.

Miller et al. (1969) "Clinical virology and viral surveillance in a pediatric group practice: The use of double–seeded tissue culture tubes for primary virus isolation," Am. J. Epidermiol.. 88:245–256.

Schindler et al., "Investigation of ELVIS Technology for use in HSV Typing of Clinical Specimens," Abstract, 11th Annual Clinical Virology Symposium, May 1, 1995, Clearwater Beach, FL.

Jollick et al., "Typing of HSV with the ELVIS HSV typing system: differential staining characteristics do not result from promoter–transactivator specificity," Abstract, 12th Annual Clinical Virology Symposium, Clearwater FL (1996).

Astier–Gin et al. (1995) "Identification of HTLV–I– or HTLV–II–producing cells by cocultivation with BHK–21 cells stably transfected with a LTR–lacZ Gene construct," J. Virological Methods 51:19–30.

Huang et al. (1998) "Application of Mixed Cell Lines for Detection of Viruses from Clinical Specimens.".

ELVIS™ Enzyme Linked Virus Inducible System, 1995 catalog page, Diagnostic Hybrids, Inc.

ATCC catalog, http://phage.atcc.org; ATCC No. CCL–64.

Kniazeff et al. (1976) "Characteristics of epithelial cells cultured from feline lung," Lab. Invest.5:495–500.

Milo et al. (1984) "Growth characteristics, morphology, and phospholipid composition of human type II pulmonary alveolar cells grown in a collagen–free microenvironment," In Vitro, 20:899–911.

Richards et al. (1987) "Isolation, biochemical characterization, and culture of lung type II cells of the rat," Lung 165:143–158.

Robinson et al. (1984) "Isolation and culture of human alveolar type II epithelial cells," Am. Rev. Respir. Disease 130:1156–1160.

Barenfanger et al. (2000) "Combination of Mixed Cell Lines Mix A and Mix B Supports Growth of All Clinical Enterovirus Isolates Tested".

Navarro–Mari et al. (1999) "Rapid Detection of Respiratory Viruses by Shell Vial Assay Using Simultaneous Culture of HEp–2, LLC–MK2, and MDCK Cells in a Single Vial," J. Clin. Microbiol. 37:2346–2347.

Huang et al. (May 9–12, 1999) Clinical Virology Symposium, "CV–1/MRC–5 mixed cells for detection of herpes simplex viruses: comparision with prinary rabbit kidney and mink lung cells".

Huang et al. (Apr. 26–29, 1998) Clinical Virology Symposium, "Sensitive cell lines for detection of respiratory viruses from primary rhesus monkey kidney and HEP–2 cells".

Huang Y.T. (Nov. 1998) "Rapid detection of respiratory viruses and enteroviruses using mixtures of continuous cells," Pan Am. Soc. Clin. Virol. 25:1–4.

Stacey Schultz–Cherry et al. (1998) "Mink Lung Epithelial Cells: Unique cell line that supports influenza A and B virus replication," J. Clin. Microbiol.36:3718–3720.

Anisimova et al, Archives of Virology 81, 223–237 (1984), "Effects of n–Butyrate and Phorbol Ester (TPA) on Induction of Epstein Barr . . . ".

Anisimova et al, J. gen. Virol. (1982), 58, 163–171, "Effects of n–Butyrate on Epstein–Barr Virus–Carrying Lymphoma Lines.".

Ash, Virology 155, 584–592 (1986), "Butyrate–Induced Reversal of Herpes Simplex Virus Restriction in Neuroblastoma Cells.".

Barin et al, Ann. Virol. (Inst. Pasteur) 1984, 135 E., 297–302, "Enhanced Production of Hepatitis B Surface Antigen by PLC/PRF/5 Hepatoma . . . ".

Bohan et al, Biochemical and Biophysical Research Comm., vol. 148, No. 3, 1987, pp. 899–905, "Sodium Butyrate Activates Human . . . ".

Bohan et al, Virology 172, 573–583 (1989), "Mutational Analysis of Sodium Butyrate Inducible Elements in the Human Immunodeficiency . . . ".

Carstea et al, Biochemical and Biophysical Res. Comm., vol. 192, No. 2, 1993, pp. 649–656, "Analogues of Butyric Acid that Increase the Expression . . . ".

Hagopian et al, Cell, vol. 12, 855–860, Nov. 1977, "Effect of n–Butyrate on DNA Synthesis in Chick Fibroblasts and HeLa Cells.".

Kawanishi et al, Virology 115, 406–409 (1981), "Epstein–Barr Virus–Induced Early Polypeptides in Raji and NC37 Cells Activated by . . . ".

Long et al, Cancer Research 40, 3886–3890, (1980), "Cell Cycle–Specific Enhancement of Type C Virus Activation by Sodium n–Butyrate.".

Luka et al, Virology 94, 228–231 (1979), "Induction of the Epstein–Barr Virus (EBV) Cycle in Latently Infected Cells by n–Butyrate.".

Prasad et al, In Vitro, vol. 12, No. 2, 1976, "Effect of Sodium Butyrate on Mammalian Cells in Culture: A Review.".

Radsak et al, Arch Virol (1989) 107:151–158, "Induction by Sodium Butyrate of Cytomegalovirus Replication in Human Endothelial Cells.".

Roubal et al, Acta Virol. 29:162–165, 1985, "Effect of n–Butyrate on Superinfection of Raji Lymphoblastoid Cell Line by Epstein–Barr Virus.".

Sadaie et al, Virology 202, 513–518 (1994), "Induction of Developmentally Programmed Cell Death and Activation of HIV by Sodium Butyrate.".

Saemundsen et al, Virology 107, 557–561 (1980), "Effect of n–Butyrate on Cellular and Viral DNA Synthesis in Cells Latently Infected . . . ".

Shadan et al, Journal of Virology, Aug. 1994, p. 4785–4796, vol. 68, No. 8, "n–Butyrate, a Cell Cycle Blocker, Inhibits the Replication of Polyomaviruses . . . ".

Sugaware et al, Virology 116, 354–358 (1982), "Epstein–Barr Virus–Related DNA–Binding Proteins Induced by n–Butyrate in P3HR–1 Cells.".

Tanaka et al, Virology 185, 271–280 (1991), "Sodium Butyrate–Inducible Replication of Human Cytomegalovirus in a Human Epithelial Cell Line.".

Wawra et al, Jour. of Virology, Jun. 1981, p. 973–981, vol. 38, No. 3, "Effect of Sodium Butyrate on Induction of Cellular and Viral DNA . . . ".

Williams; Evaluation of the Enzyme Linked Virus Inducible System (ELVIS) . . . Tenth Annual Clinical Virology Sym . . . T21: p. 146.

Gleaves et al, Journal of Clinical Microbiology, Apr. 1992, pp. 1045–1048, "Detection of Human Cytomegalovirus in Clinical Specimens by Centrifugation Culture With a Non-human Cell Line.".

Howard et al; Comparison of Embryonic Mink Lung (MvlLu) cell . . . Abstracts of 89th Annual Meeting of Amer. Soc. of Microbiol. C–2: p. 393.

* cited by examiner

METHODS OF CULTURING AND ASSAYING A VIRUS IN A SPECIMEN AND COMPOSITIONS AND CELL LINES FOR DOING THE SAME

RELATED APPLICATION DATA

This application is a continuation of under 35 U.S.C. § 371 of PCT/US96/20827, filed Dec. 27, 1996.

TECHNICAL FIELD OF THE INVENTION

This invention generally relates to the field of diagnostic virology. More particularly, the invention relates to methods for culturing and assaying a virus and diagnostic kits and cell lines for doing the same.

BACKGROUND OF THE INVENTION

Viruses and other microorganisms which infect humans, as well as other organisms, are numerous. Many of these viruses are associated with assorted clinical manifestations. Early detection of the viral etiological agents causing the clinical manifestation is desirable for effective treatment and management of the infected organism. Detection of even small concentrations of virus is desirable.

Tissue culture techniques using various cell lines are the most widely used means of assaying viruses. Numerous cell lines have been developed for culturing viruses. However, relatively few are useful because of the tendency of many cell lines to be unstable, to develop undesirable characteristics, or to be insensitive for viral growth. Accordingly, a more sensitive cell line for isolation and detection of viruses is a constant goal of diagnostic virologists.

Ideal cells for culturing viruses are cells which are sensitive for a variety of viral pathogens. However, such cell cultures have yet to be developed. Thus, several different cell cultures are required to diagnose various virus types. Such cell cultures are either primary cells or cell strains or lines arising from primary cells. Primary cells are started from cells taken directly from the tissue or organs of an organism. Primary cells are considered to be primary cells until subcultured for the first time wherein they are regarded as cell lines. Primary cells are expended by use so that a continuous supply of primary cells from new tissue from living donors is needed. This may require sacrifice of the donor. Furthermore, each new batch of primary cells poses a risk of endogenous viral, bacterial or fungal contamination.

Use of cell lines may minimize these problems. Cell lines arise from the first subculturing of primary cells. Such cell lines may be finite, i.e., are able to be subcultured only a limited number of times before senescence, or continuous, i.e., are able to be subcultured an infinite number of times. Such continuous cell lines are referred to as "established" cell lines when it is demonstrated the cell line may be subcultured indefinitely in vitro.

Recently, an improved shell vial technique has been developed for the detection of viruses from clinical specimens. This method may be combined with blind immunohistochemistry staining of the inoculated culture with viral specific antibody to identify the virus. This technique is commonly used in diagnostic virology laboratories. However, the method relies on the susceptibility of the cell line, used for virus culture, to viral infection. Low susceptibility of the cell line to viral infection results in poor diagnostic sensitivity.

Another recent advancement, polymerase chain reaction (PCR) technology, has been used to detect slow growing viruses, viruses which cannot be grown in cell culture, or viruses which are difficult to recover in cell culture from a specific specimen site. An example is herpes simplex virus from cerebrospinal fluid specimens. However, this technique detects viral nucleic acid and not infectious virus. When it is possible, the detection of infectious virus is often preferred because it correlates more with clinical manifestation. Accordingly, PCR detection of viral nucleic acid may only be indicative of the presence of remnants of a past infection or the presence of a latent infection.

The effect of butyrate on mammalian cells has been discussed. Prasad, K. N. et al, (1976) "*Effect of Sodium Butyrate on Mammalian Cells in Culture*: a Review," In Vitro 12, 125–132. The effect of sodium butyrate on various specific cell-virus interactions has also been examined. For instance between: (1) Epstein-Barr Virus/human lymphoblastoid cells, Luka, Janos et al, (1979) "*Induction of the Epstein-Barr Virus (EBV) Cycle in Latently Infected Cells by n-Butyrate,*" Virology, 94, 228–231; (2) herpes simplex virus/neuroblastoma cells, Ash, Ronald J., (1986) "*Butyrate Induced Reversal of Herpes Simplex Virus Restriction In Neuroblastoma Cells,*" Virology, 155, 584–592; (3) human endothelial cells/cytomegalovirus, Radsak, K., et al, (1989) "*Induction by Sodium Butyrate of Cytomegalovirus Replication in Human Endothelial Cells,*" Arch. Virology, 107, 151–158; and (4) human epithelial cells/cytomegalovirus, Tanaka, J. et al, (1991) "*Sodium Butyrate-Inducible Replication of Human cytomegalovirus in a Human Epithelial Cell Line,*" Virology, 185, 271–280.

International patent publication WO 89/06686 discloses use of butyric acid and salts thereof to enhance the efficiency of specific protein production by cultured eukaryotic cells.

SUMMARY OF THE INVENTION

This invention relates to a method of culturing a virus including the steps of: (A) providing cells from a cell line susceptible to infection by the virus and a specimen; (B) treating the cells with a compound of the formula RC(O)Q, wherein Q is R, OR, OX, or X, each R is independently hydrogen or a hydrocarbyl group containing 1 to about 10 carbon atoms and wherein X is hydrogen or a cation; (C) inoculating the treated cells with the specimen; and (D) incubating the inoculated cells to allow viral growth to proceed.

In accordance with another aspect of the invention is a diagnostic kit for assaying a virus includes (A) cells from a cell line susceptible to infection by the virus; (B) a compound of the formula RC(O)Q, wherein Q is R, OR, OX, or X, each R is independently hydrogen or a hydrocarbyl group containing 1 to about 10 carbon atoms and wherein X is hydrogen or a cation; and (C) reagents for assaying the virus.

In another aspect of the invention is a method for culturing a virus, comprising the steps of: (1) inoculating treated cells from a cell line susceptible to infection by the virus with the specimen, wherein the cells are treated with a compound of the formula RC(O)Q, wherein Q is R, OR, OX or X, each R is independently hydrogen or a hydrocarbyl group containing 1 to about 10 carbon atoms and wherein X is hydrogen or a cation; and (2) incubating the inoculated cells to allow viral growth to proceed.

In accordance with still another aspect of the invention is a method for assaying a virus, includes (A) providing cells from a cell line susceptible to infection by the virus and a specimen; (B) treating the cells with a compound of the formula RC(O)Q, wherein Q is R, OR, OX, or X, each R is independently hydrogen or a hydrocarbyl group containing 1 to about 10 carbon atoms and wherein X is hydrogen or a cation; (C) inoculating the treated cells with the specimen; (D) incubating the inoculated cells to allow viral growth to proceed; and (E) assaying the virus in the cells.

In accordance with a further aspect of the invention is an enhanced mink lung cell line having improved susceptibility to infection by a herpes virus prepared by treating mink lung cells identified as ATCC #CCL64 with a compound of the formula RC(O)Q, wherein Q is R, OR, OX or X, each R is independently hydrogen or a hydrocarbyl group containing 1 to about 10 carbon atoms and wherein X is hydrogen or a cation.

In another aspect of the invention, the method relates to a diagnostic kit for assaying a virus, comprising: (1) treated cells from a cell line susceptible to infection by the virus, wherein the cells have been treated with a compound of the formula RC(O)Q, wherein Q is R, OR, OX or X, each R is independently hydrogen or a hydrocarbyl group containing 1 to about 10 carbon atoms and wherein X is hydrogen or a cation; and (2) reagents for assaying the virus.

In another aspect of the invention, the method relates a method for assaying a virus, comprising the steps of: (1) inoculating treated cells from a cell line susceptible to infection by the virus, wherein the cells have been treated with a compound of the formula RC(O)Q, wherein Q is R, OR, OX or X, each R is independently hydrogen or a hydrocarbyl group containing 1 to about 10 carbon atoms and wherein X is hydrogen or a cation; and treated cells with the specimen; (2) incubating the inoculated cells to allow viral growth to proceed; and (3) assaying the virus in the cells.

The claimed methods, diagnostic kits and enhanced cell lines provide and have improved sensitivity for virus assay and enhanced susceptibility to virus infection.

DESCRIPTION OF THE PREFERRED EMBODIMENTS

The term "hydrocarbyl" includes hydrocarbon as well as substantially hydrocarbon groups. Substantially hydrocarbon groups describes groups which contain heteroatoms substituents that do not alter the predominantly hydrocarbon nature of the substituent. Examples of hydrocarbyl groups include the following:

(1) hydrocarbon substituents, i.e., aliphatic (e.g., alkyl or alkenyl) and alicyclic (e.g., cycloalkyl, cycloalkenyl) substituents, aromatic-, aliphatic- and alicyclic-substituted aromatic substituents and the like, as well as cyclic substituents wherein the ring is completed through another portion of the molecule (that is, for example, any two indicated substituents may together form an alicyclic radical);

(2) substituted hydrocarbon substituents, i.e., those substituents containing non-hydrocarbon groups which, in the context of this invention, do not alter the predominantly hydrocarbon nature of the substituent; those skilled in the art will be aware of such groups (e.g., halo, hydroxy, mercapto, nitro, nitroso, sulfoxy, etc.);

(3) heteroatom substituents, i.e., substituents which will, while having a predominantly hydrocarbon character within the context of this invention, contain an atom other than carbon present in a ring or chain otherwise composed of carbon atoms (e.g., alkoxy-or alkylthio). Suitable heteroatoms will be apparent to those of ordinary skill in the art and include, for example, sulfur, oxygen, nitrogen and such substituents as, e.g., pyridyl, furyl, thienyl, imidazolyl, etc.

In general, no more than about 2, preferably no more than 1 heteroatom substituent will be present for every 10 carbon atoms in the hydrocarbyl group. Typically, there will be no such heteroatom substituents in the hydrocarbyl group. Accordingly, the hydrocarbyl group is purely hydrocarbon.

In this specification and in the appended claims the term "isomer" is to be given its standard meaning in the art and includes, but is not limited to, both structural and optical isomers as well as other types of isomers know in the art.

In this specification and in the appended claims a "herpes virus" is meant to describe the herpesviridae viruses which include but are not limited to cytomegalovirus (CMV), Epstein-Barr virus (EBV), herpes virus 6, Varicella-Zoster virus (VZV) and herpes simplex virus (HSV). "Chiamydiae" is meant to include chlamydia psittaci, chlamydia pneumoniae and chlamydia trachomatis. "Adenoviruses" are meant to include all types of human adenovirus as well adenoviruses which infect other organisms.

In this specification and the appended claims the term "cytopathic effect (cpe)" is defined as morphological changes which are induced in the cell as a result of viral infection of the cell. Such morphological changes may be syncytial, ballooning, enlargement, round-up, etc.

It is also to be understood that, in this specification and in the appended claims, assaying includes detecting and/or quantitating as well as other means of characterization of the virus known in the art.

It is also to be understood that although the invention is described in terms of viruses, the techniques and processes of the present invention may be used for culturing and/or assaying other types of micro-organisms which may be cultured in cells. An example of such a micro-organism is chlamydiae and for purposes of this specification and appended claims such micro-organisms which can be cultured in cells are meant to be included within the scope of the term "virus" although they are not actually viruses.

The method for culturing a virus of the present invention includes the steps of: (A) providing cells from a cell line susceptible to infection by the virus and a specimen; (B) treating the cells with a compound of formula RC(O)Q, wherein Q is R, OR, OX, or X, each R is independently hydrogen or a hydrocarbyl group containing 1 to about 10 carbon atoms and wherein X is hydrogen or a cation; (C) inoculating the treated cells with the specimen; and (D) incubating the inoculated cells to allow viral growth to proceed.

Generally, the present invention may be used to culture any virus which may infect a cell line in vitro. Specific examples include but are not limited to herpes viruses, the adenoviruses, paramyxoviridae viruses, influenza viruses, enteroviruses, and chlamydiae.

In one embodiment, the virus is herpes simplex virus (HSV), including HSV-1, HSV-2, cytomegalovirus and varicella zoster virus. HSV-1 and HSV-2 belong to the genus simplex virus of the herpes virus family. The specific properties of HSV-1 and HSV-2 are variable host range, relatively short growth cycle, rapid spread in culture, efficient destruction of infected cells, and the capacity to establish latency, primarily in sensory ganglia.

In one embodiment, the virus is cytomegalovirus (CMV). CMV is a herpes virus and has typical herpes virus morphology including a large DNA genome and the ability to establish persistent and latent infections. CMV is a member of the beta-herpes group which also includes herpes virus 6 and herpes virus 7. CMV has distinguishing characteristics which include salivary gland tropism, species specificity, and slow growth in tissue culture.

In one embodiment, the virus is an adenovirus. In another embodiment, the virus is a human adenovirus. Human adenoviruses are classified in the adenovirus family and in the genus Mastaadenovirus. Adenovirus is a DNA virus and based on DNA homology, the 47 human adenovirus serotypes divide into 6 subgenera. Examples of adenoviruses include human adenovirus type 3 and adenovirus type 5.

In one embodiment, the viruses are in the family of paramyxoviridae. These viruses include genus of paramyxovirus, pneumovirus and mobilivirus. The important human pathogens of this group of viruses are respiratory syncytial virus, measles virus, parainfluenza virus type 1, 2, 3, 4, and mumps virus. The genome of this group of virus is nonsegmented, negative sense RNA. This group of viruses are transmitted via respiratory secretions through close person to person contact and aerosols. The virus initiates infection by invasion of the respiratory epithelial cells. The clinical manifestations include croup, pneumonia, bronchiolitis and common cold, and measles for measles virus and parotitis and orchitis for mumps virus. Respiratory syncytial virus is the most common lower respiratory tract infection of infants and young children. The second common one is parainfluenza virus type 3.

In one embodiment, the virus is an influenza virus. Influenza viruses belong to the family of Orthomyxoviridae, which contains influenza virus type A, influenza virus type B and influenza virus type C. The genome is segmented, single-stranded and negative sense RNA. The virus transmitted by infected respiratory secretions and replicate in the respiratory epithelial cells. The common clinical syndromes of Influenza A or B infections are fever, myalgias and cough, with clinical syndromes of common cold, pharyngitis, croup, bronchiolitis and pneumonia. Influenza A causes about 2 epidemics every 3 years and Influenza B is once every 3 years. Influenza C associates with subclinical or common cold like illness and does not cause recognized epidemics.

In one embodiment, the virus is an enterovirus. Enterovirus and rhinovirus are the two gena of the family of picornaviridae. Enteroviruses have been subdivided into polioviruses type 1-3, coxsackieviruses group A type 1-24, group B type 1-6, echoviruses type 1-34 and enteroviruses type 68-72. The virus contains a linear, single-stranded RNA genome. The RNA is infectious. Initially, ingested virus implants and replicates in susceptible tissues of the pharynx or distal part of the gut. The majority of enterovirus infections are asymptomic, but in some cases, a variety of different clinical syndromes may occur such as respiratory illnesses, aseptic meningitis, hand-foot-and-mouth disease, herpangina, acute hemorrhagic conjuncvitis, paralysis etc.

In one embodiment, the virus is chlamydiae. The chlamydiae are actually not a virus, but rather non-motile, gram-negative, obligate intracellular bacteria which may be cultured in cells. There are three species of chlamydiae: *chlamydia trachomatis, chlamydia psittaci* and *chlamydia pneumoniae*.

The cells provided are from a cell line generally characterized as being susceptible to infection by the virus to be cultured or assayed. Examples of cell lines useful in the present invention include but are not limited to mink lung cells, McCoy cells, buffalo green monkey kidney cells, human lung carcinoma A549 cells, African green monkey kidney cell line, Rhesus monkey kidney cell line (LLc mk-2), Baby hamster kidney cell line (BHK), and Human lung mucoepidermoid carcinoma cell line (NCl-H292). In one embodiment, the cell lines are nonhuman cell lines.

Mink Lung cells are available from the American Type Culture Collection (ATCC), Rockville, Md. as mink lung cell line ATCC No. CCL64. Mink lung cells are obtained from the trypsinized lungs of near term, unsexed fetuses of Aleutian minks. McCoy cells are of mouse origin and are available from ATCC as ATCC No. CRL 1696. A549 cells are lung carcinoma cells of human origin and are available from ATCC as ATCC No. CCL185. Buffalo green monkey kidney cells (BGMK) are available from BioWhittaker Co. of Walkersville, Md. African green monkey kidney cell lines are available from ATCC as the following cell lines and their corresponding catalog numbers: CV-1, CCL-70; BSC-1, CCL26; VERO, CCL 81; VERO 76, CRL 1587, VERO C-1008, CRL 1586. Rhesus monkey kidney cell line LLc mk-2 is available from ATCC as ATCC CCL-7. Baby hamster kidney cell lines are available from the ATCC as following cell lines and their corresponding ATCC catalog numbers: BHK 21, CCL10; and BHK 21C13, CRL 8544. Human lung mucoepidermoid carcinoma cell line NCl-H292 is available from ATCC as ATCC No. CRL 1848. Although the subject invention is discussed in terms of established cell lines, it is also contemplated that the methods or compositions of the invention may find use with primary cell cultures as well as non-established or finite cell lines.

In one embodiment, the cell line may be a genetically engineered cell line. In one embodiment, the cell line is selected from the group consisting of McCoy cells and BGMK cells and the virus is a chlamydiae.

The cell lines and the viruses may be used in any combination. In one embodiment, the cell line is human lung carcinoma A549 cells and the virus is an adenovirus. A549 cells are generally used to culture adenovirus because of its susceptibility to adenovirus infection. In a further embodiment, the cell line is a mink lung cell line and the virus is a herpes virus. The following chart provides further embodiments of the combiantions of cell lines and viruses.

| Virus | Cell Line |
| --- | --- |
| 1. Paramyxoviridae | African green monkey kidney cell lines |
|  | Rhesus monkey kidney cell line (LLc mk-2) |
|  | Mink lung cell line |
| 2. Influenza viruses | African green monkey kidney cell lines |
|  | Rhesus monkey kidney cell line (LLc mk-2) |
|  | Mink lung cell line |
| 3. Adenoviruses | African green monkey kidney cell lines |
| 4. Enteroviruses | African green monkey kidney cell lines |
|  | Rhesus monkey kidney cell line (LLc mk-2) |
|  | Human lung mucoepidermoid |
|  | carcinoma cell line (NCl-H292) |
| 5. Human herpes viruses | African green monkey kidney cell lines |
|  | Baby hamster kidney cell line (BHK) |
|  | Mink lung cell line. |

As recited above, a specimen is provided. The specimen provided may or may not be infected with or contain the virus. If the culturing method is to be used to provide virus for preparation of vaccine or viral proteins, etc., the specimen is pure virus or a specimen known to contain a virus.

Examples of suitable specimens for use in the present invention include body fluids, swabs, aspirates and washes from body cavities, body lesions, and various body tissues suspected of being infected with the virus or microorganism, as well as aliquots of solutions containing the virus or pure virus.

In one embodiment, the specimen is suspected of CMV infection. Examples of suitable specimens include urine, blood, eye swabs, throat swab, cerebral spinal fluid (CSF), rectal swab, bronchial wash, lung tissue, liver tissue, kidney tissue, heart tissue and brain tissue. In another embodiment, the specimen is suspected of herpes simplex virus infection. Examples of suitable specimens include vesical lesions, cervical swabs, mouth swabs, CSF, eye swabs, brain tissue, liver tissue and lung tissue. In still another embodiment, the specimen is suspected of adenovirus infection. Examples of suitable specimens include nasal swabs or expectorant, throat swabs, stool, urine, eye swabs and washings, nasopharyngeal washings and CSF. In a still further embodiment, the specimen is suspected of a chlamydia infection. Examples of suitable specimens include conjunctiva from eye infections, anterior urethra or cervix from genital infection, nasopharyngeal or tracheobronchiai-aspirates from pulmonary infection.

In one embodiment, the specimen is pure virus or other microorganism obtainable from various depositories such as the ATCC or commercial sources known in the art. In a further embodiment, the specimen is as described above and is known to contain a virus.

As described above the cell line provided is treated with a compound of formula RC(O)Q, wherein Q is R, OR, OX, or X, each R is independently hydrogen or a hydrocarbyl group containing 1 to about 10 carbon atoms and wherein X is hydrogen or a cation.

In one embodiment, R may be an alkyl, hydroxyalkyl, or haloalkyl group containing 1 to about 10 carbon atoms, or an alkoxyalkyl group containing 2 to about 10 carbon atoms. In another embodiment, R may be an alkyl group containing 1 to about 6 carbon atoms.

Specific examples of alkyl groups containing from one to about 10 carbon atoms include methyl, ethyl, propyl, butyl, pentyl, hexyl, heptyl, octyl, nonyl, decyl, cyclopentyl, cyclohexyl, 2-ethylhexyl groups as well as isomers thereof. Specific examples of hydroxyalkyl groups containing one to about 10 carbon atoms include hydroxymethyl, hydroxyethyl, and the various isomers of hydroxypropyl, hydroxybutyl, hydroxypentyl, hydroxyhexyl, hydroxyheptyl, hydroxyoctyl, hydroxynonyl, and hydroxydecyl groups. Specific examples of alkoxyalkyl groups containing two to about 10 carbon atoms include methoxymethyl, ethoxymethyl, butoxymethyl, butoxybutyl, etc. Specific examples of haloalkyl groups containing one to about 10 carbon atoms include the various isomers of chloromethyl, bromomethyl, iodomethyl, chloroethyl, bromoethyl, bromopropyl, iodoethyl, chlorobutyl, bromobutyl, iodobutyl, chloropentyl, bromopentyl, etc.

Generally, X is hydrogen or a cation. In one embodiment, X is hydrogen. In another embodiment, X is a cation. In still another embodiment, X is an alkali metal cation. In a further embodiment, X is a sodium cation. Suitable examples include but are not limited to lithium, sodium, potassium, cesium and ammonium cations.

In one embodiment, the compound of formula RC(O)Q is butyric acid and salts thereof. In another embodiment, the compound of formula RC(O)Q is sodium butyrate.

Generally, the cell line is treated with an amount of the compound of formula RC(O)Q which is sufficient to enhance the cell line susceptibility to infection by the virus. In general, the amount of the compound used to treat the cell line will vary with the cell line and virus being used. Generally, the cell lines may be treated at a concentration of about 0.1 mM up to the viability limt of the cell line. The term viability limit refers to the concentration level of the compound which is toxic to the cell line and the point at which the cell line is no longer viable for infection. The cell line would preferably be viable for at least about 12 hours, preferably from about 1 to about 30 days, more preferable from about 3 to about 15 days after treatment with the compound. In one embodiment, the cell line is treated with the above described compound at a concentration from about 0.1 mM to about 250 mM, or from about 2 to about 240 mM, or from about 5 mM to about 180 mM. In one embodiment, the cell line is treated with the compound, such as sodium butyrate, having a concentration from about 0.1 mM to about 250 mM, or from about 0.1 mM to about 200 mM or from about 1 mM to about 175 mM, or from about 2.5 mM to about 150 mM. It is to be understood that, in this specification and in the appended claims, the range and ratio limits recited herein, may be combined.

In one embodiment, the cell line is a mink lung cell line and the virus is CMV and the mink lung cell line is treated with the compound, such as sodium butyrate, having a concentration of about 40 mM to about 120 mM, or about 50 mM to about 110 mM, or about 60 mM to about 100 mM. In another embodiment, the cell line is a mink lung cell line and the virus is a herpes simplex virus and the mink lung cell line is treated with sodium butyrate having a concentration of about 0.1 mM to about 20 mM, or about 0.5 mM to about 18 mM, or about 1 mM to about 15 mM.

In one embodiment, the cell lines are those infected by the parmyxoviridae and influenza viruses, such as African green monkey kidney cell line, Rhesus monkey kidney cell line, Mink lung cell line, and Mink lung cell lines. These cell lines are treated with the compound at a concentration from about 10 mM to about 180 mM, or from about 15 mM to about 120 mM, or from about 20 mM to about 80 mM.

In another embodiment, the cell lines are those infected by the adenovirus and enterovirus, such as African green monkey kidney cell line, Rhesus monkey kidney cell line, and Human lung mucoepidermoid carcinoma cell line. These cell lines are treated with the compound at a concentration from about 0.1 mM to about 80 mM, or from about 1 mM to about 50 mM, or from about 2 mM to about 30 mM, or from about 5 mM to about 10 mM.

Generally, the sodium butyrate is prepared in a solution of tissue culture media by weighing out the appropriate amount of sodium butyrate according to the desired concentration and dissolving it in the tissue culture medium. However, it is to be understood that the compound of formula RC(O)Q may be prepared in a solution of any solvent or solution which will not inhibit or otherwise negatively impact upon viral growth. For example, the sodium butyrate may be prepared in water.

The tissue culture media used is generally any media which will support cell culture. For instance, the tissue culture medium may be Opti-MEM which is available from Life Technologies, Inc. of Gaithersburg, Md. Opti-MEM is a modification of Minimum Essential Medium (MEM), buffered with 4-(2-hydroxyethyl)-1-piperazine ethane sulfonic acid (HEPES) and sodium bicarbonate and supplemented with hypoxanthine, thymidine, sodium pyruvate, L-glutamine, trace elements and growth factors. MEM generally contains inorganic salts, D-glucose, phenol red sodium succinate, succinic acid, amino acids and vitamins.

The cells of the cell line are generally treated with the compound of Formula I for a time sufficient to allow enhancement of cell line susceptibility to viral infection. In one embodiment, the cells are treated from about 1 hour to about 72 hours, or from about 8 hours to about 56 hours, or from about 12 hours to about 36 hours, with the compound of formula RC(O)Q.

Once treated the cells are inoculated with a specimen, described above, which is suspected of being or known to be infected by the virus or the cell line may be inoculated with the actual virus. Inoculation is accomplished by contacting the specimen with the treated cells and is done by any technique know in the art which will effectively contact the specimen with the cell line.

The specimen inoculum is prepared as follows. Clinical specimens are collected from an infected site such as the throat, nose, vesicle lesions, urine, etc., and put into a viral transport medium. Any viral transport media known in the art may be used. Generally, such media contain a buffer, protein and various antibiotics and/or fungizones such as penicillin, streptomycin, amphotericin, etc. The transport media mixture is generally vortexed and filtered through a membrane to eliminate contamination. At this point the inoculum is ready to be inoculated into the cell culture.

After inoculation, the inoculated cells are incubated to allow viral growth or infection to proceed. In one embodiment, the inoculated cells are incubated from about 1 hour to about 72 hours, or from about 8 hours to about 56 hours, or from about 12 hours to about 36 hours at a temperature conducive to viral growth. In one embodiment, the inoculated cells are incubated from about 25° C. to about 50° C., or about 30° C. to about 45° C., or from about 35° C. to about 40° C. In one embodiment, the incoculated cells are incubated at about 37° C.

In another embodiment, the culturing method may include a further step (E) harvesting said virus. The harvested virus can be used in the production of vaccines, viral proteins, viral antigens, antibodies, etc. The viruses are harvested according to methods known in the art depending on the specific character of the virus and the cells in which they are grown. For viruses which are released into the tissue culture medium, the viruses are collected at the peak of cytopathic effect. Generally, the virus containing medium is collected. If cells or cell remnants remain in the medium, the medium may be centrifuged to pellet the cell material for removal. For viruses which are cell associated and do not release efficiently into the tissue culture medium, the cell as well as the medium needs to be harvested. The cell is then sonicated or quick-frozen and thawed to release the virus from the cells. The cell debris is then pelleted and removed by centrifugation. Subsequently, most viruses are generally stable when stored at about −70° C.

In another aspect of the invention a method for assaying a virus in a specimen is contemplated. The method includes the steps of (A) providing cells from a cell line susceptible to infection by the virus and a specimen; (B) treating the cell line with a compound of formula RC(O)Q, wherein Q is R, OR, OX, or X, each R is independently hydrogen or a hydrocarbyl group containing 1 to about 10 carbon atoms and wherein X is hydrogen or a cation; (C) inoculating the treated cells with the specimen; (D) incubating the inoculated cells to allow viral growth to proceed; and (E) assaying the virus grown in the cells.

Steps (A), (B), (C) and (D) as well as the compositions and components used therein are as described above. In step (E) the virus is assayed in the specimen using any suitable method known in the art. Examples of such methods include tube culture, shell vial, PCR, Elisa and direct antigen staining.

In one embodiment, the virus is assayed by immunofluorescent staining. Generally, immunofluorescent staining involves staining the infected cells with an antibody or antibodies directed to a particular antigen produced by the virus. A fluorescent compound is attached to the antibody or to a related compound so that when the antigen-antibody complex is formed viral presence is visualized. The fluorescence tagged antibody-antigen complex is viewed using a fluorescence equipped microscope.

The following examples illustrate the processes and compositions of the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

Mink lung cells available from American Type Culture Collection ATTC No. CCL64 are provided. The cells are received in frozen vials from ATCC and are prepared by first thawing in a 37° C. water bath. The thawed cells are removed from the bath and cultured in a tissue culture flask with Opti MEM culture medium supplemented with 5% fetal calf serum and non-essential amino acids, available from Life Technologies, Inc., of Gaithersburg, Md., and the antibiotics penicillin (100 units/ml), streptomycin (100 $\mu$g/ml) and the fungizone amphotericin (0.25 $\mu$g/ml). The cultured cells reach a complete monolayer in about 3 to 4 days. The mink lung cells are propagated by trypsinization and approximately $2.5 \times 10^5$ dispersed cells per shell vial are seeded in shell vials with cover slips. The shell vials are incubated at 37° C. for 24 hours or until the cells form a monolayer.

The cells were then treated with a 5 mM sodium butyrate (NaB) tissue culture solution, prepared by dissolving the appropriate amount of NaB in tissue culture media and filtering the solution, and incubated for 16 to 24 hours. After incubation the NaB and tissue culture media is removed and the treated cells are inoculated with 0.2 ml of CMV inoculum originally from a clinical specimen obtained from urine and prepared by putting the specimen into a viral transport medium containing Hank's buffer, 1% bovine albumin and the antibiotics penicillin (200 units/ml) and streptomycin (200 $\mu$g/ml) and the fungizone amphotericin (0.5 $\mu$g/ml). After inoculation the shell vials are centrifuged at 700×g for 45 minutes at 23° C. After centrifugation, 0.5 ml of fresh media is added to each vial and the vials are incubated at 37° C. for 16 to 24 hours. After incubation the media is removed and the cell layers are rinsed with phosphate buffered saline (PBS), fixed with cold acetone for 10 minutes, and rinsed again with PBS.

After fixing, the cells are stained by adding 100 $\mu$l of CMV monoclonal antibody (mAb), incubated at 37° C. for 45 minutes and then rinsed with PBS. The CMV mAb used is E-13 monoclonal antibody against immediate early (IE) antigen of CMV. This antibody is used as a primary antibody in the first step of staining and is available from Accurated Chemical and Scientific Co., Westbury, N.Y. After the first staining step 100 $\mu$l of biotin which is conjugated with antimouse IgG is added followed by additional incubation at 37° C. for 45 minutes. The biotin complex is available from Boerhinger Mannheim Co., Indianapolis, Ind. The cells are rinsed again with PBS after incubation and then incubated with 100 $\mu$l of streptavidin conjugated with fluorescein isothiocyanate (FITC) for 45 minutes at 37° C. The streptavidin complex is also available from Boerhinger Mannheim Co., Indianapolis, Ind. After a final rinse with PBS, a coverslip removed from the shell vial is mounted on the slide which is then examined under a fluorescence equipped microscope manufactured in Germany by Carl Zeiss, Inc., and available from W. Nuhsbaum, McHenry, Il. The specific apple-green stained nuclei were counted. The results are reported in Table 1 as positive stained nuclei as an average of four shell vials.

EXAMPLES 2–6

These examples used the same procedure as Example 1, except that the concentration of NaB used was different. Table 1 indicates the concentration of NaB used and the results.

Conventionally, human embryonic lung (HEL) fibroblast cells, such as the MRC-5 cell line which is available from Diagnostic Hybrids, Inc., Athens, Ohio, are used worldwide for CMV culture and viral isolation.

Comparative Example 1

This example used the same procedure as Example 1 except the CMV was grown in MRC-5 cells. The MRC-5 cells were not treated with NaB before infection, but were treated with 2 mM calcium chloride (CaCl$_2$), 1% dimethyl sulfoxide (DMSO) and 10$^{-5}$ M dexamethasone after infection. The results are reported in Table 1.

TABLE 1

| Ex. | NaB (mM) | # positive stained nuclei |
|---|---|---|
| 1 | 5 | 22 |
| 2 | 10 | 30 |
| 3 | 20 | 38 |
| 4 | 40 | 71 |
| 5 | 80 | 85 |
| 6 | 0 | 8 |
| COMP EX 1 | MRC-5 cells | 9 |

As seen from Table 1, untreated mink lung cells, are slightly less sensitive than MRC-5 cells for CMV isolation and detection. However, when treated with NaB, mink lung cells show far superior sensitivity for CMV isolation and detection. The number of stained cells increases as the concentration of NaB is increased up to 80 mM with the increase being about 10 fold as compared with untreated mink lung cells.

EXAMPLES 7–11

Mink lung cells were prepared as described in Example 1. The mink lung cells were treated with various concentrations of sodium butyrate for 16 to 24 hours as indicated in Table 1. Cells were then infected with HSV-1 (originally from clinical specimens but passaged once in tissue culture so virus content is assured). The HSV-1 culture fluid was diluted 1:1000 before use for inoculation. In each shell vial, 0.2 ml of inoculum was used. After centrifuging for 45 minutes at 700×g at 23° C., 0.5 ml of Opti-MEM with 2% fetal calf serum was added to each vial and incubated overnight at 37° C. The following day, the cytopathic effect of the inoculated culture was observed under light microscope. The results are reported in Table 2 and are from the average of two shell vials.

Cell culture isolation and detection of HSV-1 from clinical specimens is conventionally done using primary rabbit kidney (RK) cells. RK cells are available from Biowhittaker Co., Walksville, Md. However, RK cells are primary cells so that animals need to be sacrificed each time cells are prepared. Consequently, the procedure for obtaining the cells is quite tedious and costly.

Comparative Example 2

This example used the same procedure as Example 7 except that rabbit kidney cells were used to grow the virus and the RK cells were not treated with NaB. The results are reported in Table 2.

TABLE 2

| Ex. | NaB (mM) | cpe[1] |
|---|---|---|
| 7 | 2.5 | 18 |
| 8 | 5.0 | 20 |
| 9 | 10.0 | 22 |
| 10 | 20 | 12 |
| 11 | 0 | 6 |
| Comp Ex 2 | RK cels | 26 |

[1]cpe = foci of cytopathic effect

As seen from Table 2, untreated mink lung cells, are less sensitive than RK cells for HSV-1 isolation and detection. However, when treated with NaB, mink lung cells show comparable sensitivity for HSV isolation and detection. Also, Table 2 shows that in comparison to growth of CMV in mink lung cells wherein the optimum concentration appears to be about 80 mM, for HSV-1 growth optimum concentration is shown to be about 5 mM to about 10 mM.

EXAMPLES 12–21

These examples were prepared using the same procedure as Example 1, except that the concentration of NaB used was varied and both mink lung cells and MRC-5 cells were used. Also, the MRC-5 were treated with NaB before infection and 2 mM CaCl$_2$, 1% DMSO and 10$^{-5}$M dexamethasone after infection. Table 3 indicates the concentration of NaB used and the results obtained.

TABLE 3

| Ex. | NaB- (mM) | Mink lung cells # of stained nuclei | MRC-5 cells # of stained nuclei |
|---|---|---|---|
| 12 | 0 | 1 | 1 |
| 13 | 0 | 6 | 2 |
| 14 | 10 | 7 | 2 |
| 15 | 10 | 9 | 3 |
| 16 | 20 | 12 | 2 |
| 17 | 20 | 12 | 2 |
| 18 | 40 | 12 | 4 |
| 19 | 40 | 23 | 9 |
| 20 | 80 | 26 | 7 |
| 21 | 80 | 32 | 6 |

As seen from Table 3, mink lung cells show a better response to NaB treatment, resulting in a greater sensitivity to CMV infection, than the conventionally utilized, NaB treated, MRC-5 cells.

EXAMPLES 22–27

These examples used the same procedure as Example 1 for CMV growth except that the age of the cells were varied, the cells were treated with 80 mM sodium butyrate 24 hours before infection, and the MCR-5 cells were treated 2 mM calcium chloride (CaCl$_2$), 1% dimethyl sulfoxide (DMSO) and 10$^{-5}$M dexamethasone after infection. Also, before infection the inoculum was diluted with Opti-MEM as indicated in Table 4. The results are reported in Table 4.

TABLE 4

| Ex. | Cell Type | Cell Age | $10^{-0}$ | $10^{-1}$ | $10^{-2}$ |
|---|---|---|---|---|---|
| 22 | Mink Lung* | 2 days | 232/220 | 44/52 | 5/2 |
| 23 | Mink Lung | 2 days | 28/48 | 4/2 | 1/0 |
| 24 | Mink Lung* | 3 days | 242/309 | 47/43 | 1/2 |
| 25 | Mink Lung | 3 days | 28/29 | 4/2 | 2/0 |
| 26 | MRC-5* | 2 days | 39/29 | 3/1 | 0/0 |
| 27 | MRC-5 | 2 days | 20/22 | 1/1 | 1/0 |

In Table 4 * indicates cells treated with sodium butyrate, $10^{-0}$ indicates no dilution, $10^{-1}$ indicates 1:10 dilution, $10^{-2}$ indicates 1:100 dilution and the two numbers indicate counts of positive stained nuclei from 2 shell vials. The Examples of Table 4 show the effects of cell age as well as virus concentration on viral growth. It is clear from Table 4 that even at a high dilution, i.e., low concentration of virus in the inoculum, the virus is still detected when the cells are treated with NaB. In contrast, untreated mink lung cells and both treated and untreated MRC-5 cells at times show no virus detected at high dilution.

EXAMPLES 28–32

These examples used the same procedure as Example 1 for CMV growth except that the age of the cells were varied, the cells were treated with 80 mM sodium butyrate 24 hours before infection, and the MRC-5 cells were treated 2 mM calcium chloride ($CaCl_2$), 1% dimethyl sulfoxide (DMSO), and $10^{-5}$M dexamethasone after infection. The results are reported in Table 5. The cell age is measured as the time after seeding of the cells in the shell vial.

TABLE 5

| Ex. | Cell Type | Cell Age | Treated | Untreated |
|---|---|---|---|---|
| 28 | Mink Lung | 2 days | 123* | 11 |
| 29 | Mink Lung | 3 days | 121 | 10 |
| 30 | Mink Lung | 5 days | 78 | 4 |
| 31 | Mink Lung | 7 days | 30 | 2 |
| 32 | MRC-5 | 4 days | 4 | 3 |

*average # of nuclei staining from three shell vials

As shown in Table 5, 2 and 3 day old mink lung cells show greater sensitivity to CMV growth than 5 to 7 day old mink lung cells. Furthermore, NaB treatment enhanced the susceptibility of the mink lung cells to CMV infection despite the age of the mink lung cells.

EXAMPLES 33–39

These examples used the same procedure as Example 1 for CMV growth except that the time of treatment with sodium butyrate was varied, i.e., the cells were treated with 80 mM sodium butyrate for different times before infection, and the MRC-5 cells were treated with 2 mM calcium chloride ($CaCl_2$), 1% dimethyl sulfoxide (DMSO) and $10^{-5}$M dexamethasone after infection. The results are reported in Table 6.

TABLE 6

| Ex. | Cell Type | Time of Treatment | # of Foci |
|---|---|---|---|
| 33 | Mink Lung | 18 hours | 360* |
| 34 | Mink Lung | 8 hours | 306 |
| 35 | Mink Lung | 6 hours | 276 |
| 36 | Mink Lung | 4 hours | 234 |
| 37 | Mink Lung | 2 hours | 126 |
| 38 | Mink Lung | Untreated | 48 |
| 39 | MRC-5 | Untreated | 30 |

*average # of stained nuclei counted from three shell vials.

The results of Table 6 indicate that as short as a 2 hour treatment of mink lung cells with NaB, more than a two fold enhancement of CMV expression can be detected. However, for optimum enhancement at least 8 hours of treatment is required.

In another aspect of the invention a diagnostic kit for assaying a virus, includes (A) cells from a cell line susceptible to infection by the virus; (B) a compound of formula RC(O)Q, wherein Q is R, OR, OX or X, each R is independently hydrogen or a hydrocarbyl group containing 1 to about 10 carbon atoms and wherein X is hydrogen or a cation; and (C) reagents for assaying the virus is contemplated.

The cell line, virus and compound of formula RC(O)Q are as described above. The reagents for assaying the virus can be any reagents know in the art which are used to assay viruses. Examples include but are not limited to immunological, calorimetric, fluorescent, optical, etc. In one embodiment, the reagents are immunofluorescent reagents such as those described above. Examples include but are not limited to FITC-mAb to HSV-1 or HSV-2 (described above) and the E-13 mAb against immediate early antigen of CMV/biotin conjugated anti-mouse IgG/streptavidin-FITC conjugate system described above.

In still another aspect of the invention an enhanced mink lung cell line having improved susceptibility to infection by a herpes virus prepared by treating mink lung cells identified as ATCC #CCL64 with a compound of formula RC(O)Q, wherein Q is R, OR, OX or X, each R is independently hydrogen or a hydrocarbyl group containing 1 to about 10 carbon atoms and wherein X is hydrogen or a cation; is contemplated.

The mink lung cells and compound of formula RC(O)Q are as described above. The enhanced mink lung cells are prepared by obtaining mink lung cells ATCC No. CCL64 from the ATTC. The cells are received in frozen vials from ATCC and are prepared by first thawing in a 37° C. water bath. The thawed cells are removed from the bath and cultured in a tissue culture flask with Opti MEM culture medium supplemented with 5% fetal calf serum and nonessential amino acids, available from Life Technologies, Inc., of Gaithersburg, Md., and the antibiotics penicillin (100 units/ml), streptomycin (100 μg/ml) and the fungizone amphotericin (0.25 μg/ml). The cultured cells reach a complete monolayer in about 3 to 4 days. The mink lung cells are propagated by trypsinization and approximately $2.5 \times 10^5$ dispersed cells per shell vial are seeded in shell vials with cover slips. The shell vials are incubated at 37° C. for 24 hours or until the cells form a monolayer.

The cells are then treated with an appropriate concentration of sodium butyrate (NaB) prepared by dissolving the appropriate amount of NaB in tissue culture media and filtering the solution, and incubated for 16 to 24 hours.

Although the invention is described herein as being directed towards use in diagnosing viral presence, it is contemplated that any process or method, compound, composition, etc., which requires growth or culturing of viruses may find the present invention useful. For instance, the production of viral vaccines or viral proteins which may require culturing of the virus.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method for culturing a Influenza virus, comprising the steps of:
   (A) providing cells from a Mink lung cell line susceptible to infection by the virus and a specimen;
   (B) treating the cells with a compound of the formula RC(O)Q, wherein Q is R, OR, OX or X, each R is independently hydrogen or a hydrocarbyl group containing 1 to about 10 carbon atoms and wherein X is hydrogen or a cation;
   (C) inoculating the treated cells with the specimen; and
   (D) incubating the inoculated cells to allow viral growth to proceed.

2. The method of claim 1, further comprising a step (E) harvesting said virus.

3. The method of claim 1, wherein R is an alkyl, hydroxyalkyl, alkoxyalkyl, or haloalkyl group.

4. The method of claim 1, wherein Q is OX and X is hydrogen or an alkali metal cation.

5. The method of claim 3, wherein Q is OX and X is hydrogen or an alkali metal cation.

6. The method of claim 1, wherein the compound of the formula RC(O)Q is butyric acid or salts thereof.

7. An enhanced mink lung cell line having improved susceptibility to infection by a Influenza virus prepared by treating mink lung cells identified as ATCC #CCL64 with a compound of the formula RC(O)Q, wherein Q is R, OR, OX or X, each R is independently hydrogen or a hydrocarbyl group containing 1 to about 10 carbon atoms and wherein X is hydrogen or a cation.

8. The mink lung cell line of claim 7, wherein the compound of formula RC(O)Q is butyric acid or salts thereof.

* * * * *